United States Patent
Arnissolle

[19]

[11] Patent Number: 6,106,496
[45] Date of Patent: Aug. 22, 2000

[54] BALLOON INFLATING DEVICE

[75] Inventor: Yves Arnissolle, Saint Genis-Laval, France

[73] Assignee: Socite d'Etudes et d'Applications Tech, Trigny, France

[21] Appl. No.: 09/094,599

[22] Filed: Jun. 15, 1998

[30] Foreign Application Priority Data

Jun. 16, 1997 [FR] France .................................. 97 07447

[51] Int. Cl.[7] .................................................. A61M 29/00
[52] U.S. Cl. .............................. 604/97; 604/207; 604/211
[58] Field of Search ............................... 604/97–99, 100, 604/207, 208, 211, 209, 210

[56] References Cited

U.S. PATENT DOCUMENTS

| | | |
|---|---|---|
| 4,583,974 | 4/1986 | Kokernak . |
| 4,632,669 | 12/1986 | Phipps, Sr. et al. . |
| 4,654,027 | 3/1987 | Dragan et al. . |
| 4,655,749 | 4/1987 | Fischione . |
| 4,710,179 | 12/1987 | Haber et al. . |
| 4,713,061 | 12/1987 | Tarello et al. . |
| 4,723,938 | 2/1988 | Goodin et al. . |
| 4,743,230 | 5/1988 | Nordquest . |
| 4,808,165 | 2/1989 | Carr . |
| 4,832,692 | 5/1989 | Box et al. . |
| 4,838,864 | 6/1989 | Peterson . |
| 4,919,121 | 4/1990 | Rydell et al. . |
| 4,929,238 | 5/1990 | Baum . |
| 4,940,459 | 7/1990 | Noce . |
| 5,057,078 | 10/1991 | Foote et al. . |
| 5,137,514 | 8/1992 | Ryan ......................................... 604/99 |
| 5,147,300 | 9/1992 | Robinson et al. ......................... 604/97 |
| 5,160,327 | 11/1992 | Stines . |
| 5,168,757 | 12/1992 | Rabenau et al. . |
| 5,209,732 | 5/1993 | Lampropoulos et al. . |
| 5,213,115 | 5/1993 | Zytkovicz et al. . |
| 5,279,563 | 1/1994 | Brucker et al. . |
| 5,284,480 | 2/1994 | Porter et al. . |
| 5,290,260 | 3/1994 | Stines . |
| 5,318,534 | 6/1994 | Williams et al. . |
| 5,342,304 | 8/1994 | Tacklind et al. .......................... 604/99 |
| 5,433,707 | 7/1995 | Call . |

FOREIGN PATENT DOCUMENTS

| | | |
|---|---|---|
| 217559 | 2/1990 | European Pat. Off. . |
| 0565045 | 4/1993 | European Pat. Off. . |
| 565045 | 10/1993 | European Pat. Off. . |
| 463111 | 3/1994 | European Pat. Off. . |
| 92/17221 | 10/1992 | WIPO . |

*Primary Examiner*—Wynn Wood Coggins
*Assistant Examiner*—Jennifer R. Sadula
*Attorney, Agent, or Firm*—Sughrue, Mion, Zinn, Macpeak & Seas, PLLC

[57] ABSTRACT

The balloon inflating device comprises a syringe (12) the plunger (28) of which has a screw thread (36). It further comprises a mechanism for retaining the plunger comprising a first half nut (40A) movable between a position separated from the screw thread (36) and a position of engagement with the screw thread (36), and a slidable control element (42) which comprises first coupling means (54A) adapted to displace the first movable half nut (40A). The retaining mechanism (14) further comprises a second movable half nut (40B) movable between a position spaced away from the screw thread (36) and a position of engagement with the screw thread (36). The control element (42) further comprises second coupling means (54B) associated with the second half nut (40B) and adapted to move the second half nut. The first and second coupling means (54A, 54B) are mechanically connected to each other in the region in which the control element (42) is coupled to the first and second half nuts (40A, 40B).

10 Claims, 2 Drawing Sheets

BALLOON INFLATING DEVICE

The present invention relates to a device for inflating balloons of the type comprising a syringe including a syringe body and a syringe plunger slidably and rotatably mounted in said syringe body, the plunger having an outer screw thread on at least a part of its length, the device further comprising a mechanism for retaining the plunger comprising on one hand a first half nut movable between a position spaced from the screw thread in which the plunger is free to slide in the syringe body and a position of engagement with the screw thread in which the free sliding of the plunger is impossible and the plunger can be screwed or unscrewed in the syringe body, and on the other hand a control element mounted to be axially slidable along the syringe body, said control element comprising first coupling means adapted to move the first half nut between its two positions upon the shifting of said control element.

Such an inflating device is disclosed for example in the U.S Pat. No. 5,147,300.

A baloon inflating device is employed for injecting a fluid into a balloon previously disposed in the contracted state in an artery or a vein of a patient. Such devices are in particular employed for the purpose of percutaneous transluminal angioplasty, and in particular for dilating the artery or the vein in which the balloon is disposed.

The inflating devices must be capable of providing a high pressure of the order of 30 bars. Under the effect of such a pressure, the plunger is subjected to a considerable axial force which, in the absence of a manual pressure exerted on the free end of the plunger, must be resisted by the half nut in cooperation with the thread.

Under these conditions, it is found that the rod of the plunger bends and sometimes causes the release of the plunger by an accidental disengagement of the half nut.

Further, in the device described in said U.S patent, the element controlling the half nut is formed by a rod whose end is deformed in the shape of a crank. This end is engaged in an opening in the half nut for laterally moving the latter.

Owing to the high pressure prevailing inside the syringe which exerts a considerable axial thrust on the plunger, the release of the half nut requires a considerable force so that the control element has a tendency to deform without performing in a satisfactory manner its function of moving the half nut. Moreover, it is necessary to make the control element of an extremely rigid material which increases the manufacturing cost of the device.

An object of the invention is to provide a device for inflating balloons in which the rod is reliably retained and easy to place in position and release, while it permits the use of cheap ordinary materials.

For this purpose, the invention provides a device for inflating balloons of the aforementioned type, characterized in that the retaining mechanism comprises a second movable half nut disposed substantially symmetrically with the first movable half nut relative to the plunger, said second half nut being movable simultaneously with the first half nut between a position spaced from the screw thread and a position of engagement with the screw thread, and said control element comprises second coupling means associated with the second half nut and adapted to move the second half nut, the first and second coupling means being mechanically connected to each other in the region in which said control element is coupled to the first and second half nuts.

According to particular embodiments of the invention, the balloon inflating device may have one or more of the following features:

said first and second coupling means each comprise a part of a cam/cam follower arrangement, the complementary part being carried by the first and second half nut respectively;

the first and second coupling means comprise for each half nut at least one slot forming a cam defined in said control element and the first and second half nuts each comprise at least one pin forming a cam follower slidable in the or each associated slot;

the first and second half nuts are movable solely laterally relative to the plunger;

two slots associated respectively with the first and second half nuts are defined in a common plate of said control element, which plate extends in a direction substantially parallel to the plane of movement of the first and second half nuts;

said control element comprises two plates disposed laterally on opposite sides of the first and second half nuts, each plate comprising two slots associated with the first and second half nuts, said half nuts each comprising on each side the pins, forming cam followers, slidable in said slots;

said control element comprises two control buttons which are disposed laterally symmetrically on opposite sides of the length of the syringe body and are manually shiftable for shifting said control element;

the control buttons are provided at the end of connecting arms extending from said plates;

the screw thread comprises a thread having a substantially triangular section, the inclination relative to the perpendicular to the plunger of the front flanks of the screw thread facing towards the end of the plunger received in the syringe body being greater than the inclination of the rear flanks of the screw thread, this latter inclination being non-zero, and the inflating device comprises a pressure gauge connected to the chamber of the syringe.

A better understanding of the invention will be had from the following description which is given by way of example with reference to the accompanying drawings, in which.

Figure 1:
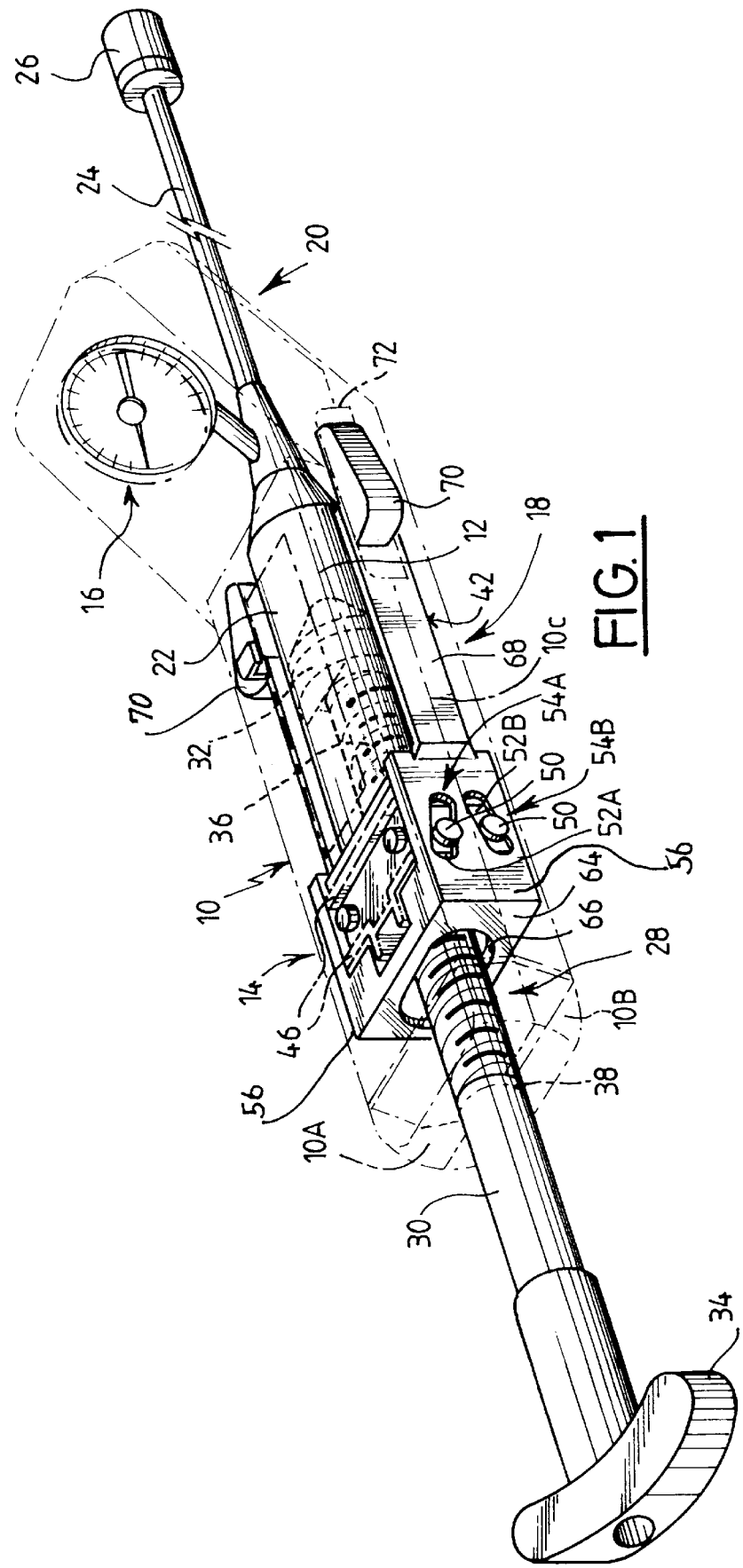
FIG. 1 is a perspective view of the device according to the invention.

The balloon inflating device shown in FIG. 1 mainly comprises a housing 10, a syringe 12 mounted in the housing, a mechanism 14 for retaining the plunger and a pressure gauge 16.

The housing 10 is made of a transparent plastics material and comprises two semi-shells, 10A, 10B, assembled with each other along a peripheral longitudinal joint line 10C. The housing has an elongate main part 18 forming a body, the front end of which is provided with an inclined extension 20 forming a transparent bracket for receiving the pressure gauge 16.

The syringe 12 comprises a syringe body 22 made of a transparent plastics material. The syringe advantageously defines a volume of 30 cm$^3$. The syringe body 22 is fixed inside the housing 10. The front end of the syringe extends out of the housing below the bracket 20. Fixed to this end is a nozzle 24 provided with a connecting terminal 26 for connection to a catheter provided with a balloon.

The syringe 12 further comprises a plunger 28 formed by a rod 30 provided at its end received inside the syringe body 22 with a head 32 slidably mounted in a sealed manner in the syringe body. The rod 30 has at its other end a handle 34 for the manual actuation of the plunger. The rod 30 of the plunger is provided with a screw thread 36 in at least a part of its length.

As shown in FIG. 1, the plunger rod 30 extends through a rear end wall of the housing through an opening 38 so that the handle 34 is accessible outside the housing.

Figure 2:
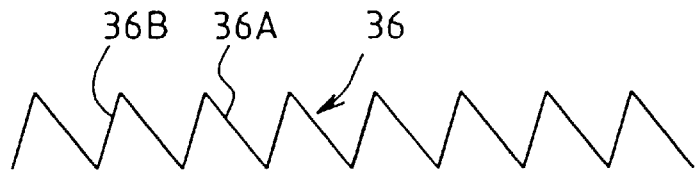
FIG. 2 is a semi-longitudinal sectional view of the screw thread of the syringe plunger.

The detail of the form or profile of the screw thread 36 is shown in FIG. 2.

The thread formed helically on the rod 30 has a triangular cross-sectional shape. The front flank 36A facing towards the end of the plunger engaged in the syringe body has an inclination relative to the perpendicular to the thread cyclinder which is greater than the non-zero inclination of the rear flank 36B facing towards the handle 34. The rear flank 36B makes for example an angle of 15° with the perpendicular while the front flank makes with this perpendicular an angle of 47°.

The plunger retaining mechanism 14 is received inside the housing 10. It mainly comprises two retaining half nuts 40A, 40B and an element 42 for controlling these two half nuts. The control element 42 is mounted to be axially slidable in the housing 10 in the direction of the length of the syringe body.

Figures 3, 4:
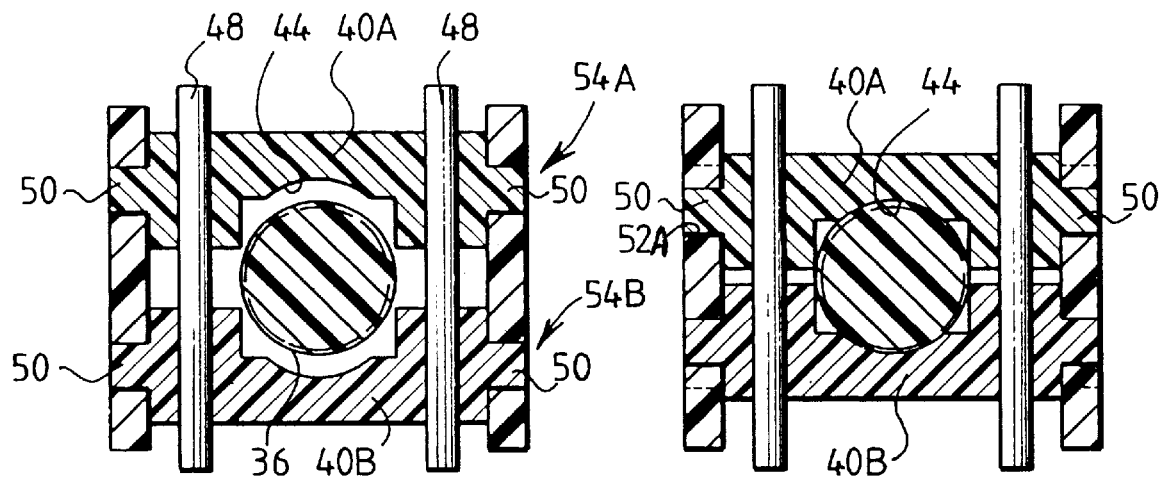
FIGS. 3 and 4 are partial cross-sectional views of the locking mechanism in the plane of the locking half nuts.

The two half nuts 40A, 40B shown in FIGS. 3 and 4 are identical and include a semi-cyclindrical open recess the surface 44 of which is tapped. The half nuts 40A, 40B are disposed symmetrically on opposite sides of the rod 30, the tapped surfaces 44 facing towards the screw thread 36 of the rod.

The half nuts 40A, 40B are axially immobilized in the housing by transverse ribs 46 extending on opposite sides of the half nut. These ribs 46 are in one piece with the housing. Further, the half nuts 40A, 40B are slidably mounted on two rods 48 which extend through the half nuts in a direction parallel to each other and perpendicular to the axis of the rod 30, between the two semi-shells 10A, 10B. In this way, the two half nuts are movable solely laterally relative to the axis of the plunger 28.

Lastly, each half nut 40A, 40B includes laterally on each side a pin 50 received in slots 52A, 52B provided in the control element 42.

The slots 52A, 52B form coupling means 54 associating the control element 42 with the first and second half nut 40A, 40B respectively. They are provided on each side of the element 42 and defined on each side in a common plate 56.

Figure 5:
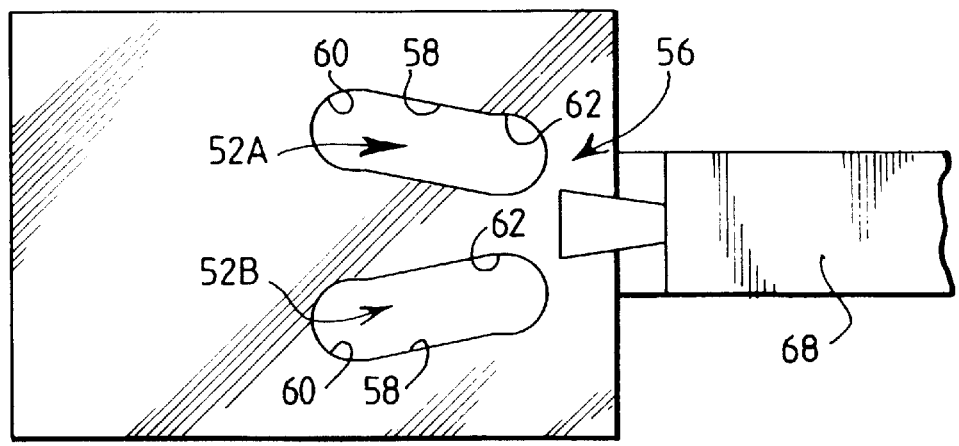
FIG. 5 is a partial side elevational view of a detail of the control element.

The two slots 52A, 52B of the same plate 56 are shown in detail in FIG. 5. The two slots have an oblong shape and extend substantially along the length of the syringe. They are convergent in the direction towards the front end of the syringe. Their width is equal to the diameter of the pins 50 received therein.

The slots have an inclined main portion 58 extended at each end by a non-inclined planar part 60, 62 respectively corresponding, for the two half nuts 40A, 40B, to a position spaced from the plunger and a position of engagement with the screw thread of the plunger.

The two plates 56 extend in a direction parallel to each other on opposite sides of the rod 30. They are connected at the rear by a transverse member 64 in one piece with the plates. This transverse member 64 is provided with an opening 66 for the passage of the plunger 28. Further, the plates 56 are extended alongside the syringe body 22 by legs 68 extending in a direction parallel to each other inside the housing 10.

At their free end, the legs 68 carry projections 70 forming control buttons. These control buttons extend laterally out of the housing in the front part of the latter. They extend through the housing through longitudinal openings 72 provided in the lateral walls of the housing.

When the buttons 70 are in the front part of the openings 72 (i.e. shifted towards the pressure gauge 16), the pins 50 are received in the planar portion 60 of the slots. Under these conditions, as shown in FIG. 3, the half nuts 40A, 40B are spaced away from the screw thread 36 so that the plunger 28 is free to slide axially in the syringe body 22. This position permits putting the fluid contained in the syringe under a prior pressure merely by depressing the plunger 28.

On the other hand, when the buttons 70 are brought to the rear part of the opening 72, the pins 50 are received in the planar portion 62 of the slots so that, as shown in FIG. 4, the half nuts 40A, 40B are engaged on the screw thread 36 which they retain and thereby prevent the free displacement of the plunger and solely allow the screwing or unscrewing of the plunger in the nut formed by the assembled half nuts 40A, 40B cooperating with the screw thread.

In order to inflate a balloon, the operator first of all releases the plunger rod and urges the rod into the syringe body so as to increase the pressure of the fluid up to a pressure of around 3 bars, which corresponds to the pressure which may be obtained merely by exerting a thrust on the plunger. Thereafter, the operator engages the half nuts 40A, 40B on the screw thread by shifting the control element 42 rearwardly. The pins 50 then travel along the slopes defined by the slots which causes, by a camming effect, the two half nuts to move towards each other. The operator then continues to increase the pressure by gradually screwing the plunger into the syringe body up to a pressure which may reach 30 bars.

In the syringe described hereinbefore, the presence of the two symmetrically arranged half nuts 40A, 40B prevents any bending of the plunger rod.

Further, the coupling means formed by the slots provided in the control element and associated with the two half nuts are mechanically interconnected since they are carried by a common plate on each side of the half nuts. Moreover, this connection occurs in the region in which the control element is coupled to the two half nuts.

In this way, as the slots are each stressed in opposite directions by a half nut, the stresses to which the plates are subjected are cancelled out so that the control element is not urged against the housing when putting the device under pressure. This also avoids deformation of the control element. This feature moreover permits an easy unlocking of the plunger rod when a high pressure prevails in the syringe.

Lastly, the presence of two control buttons 70, each provided on a lateral side of the housing, renders the device invariable in operation when it is turned round the longitudinal axis of the syringe. Consequently, whatever the direction in which the housing is held in the hand, at least one of the two buttons can be actuated by the thumb of the operator.

Further, as the control element is actuated by the two buttons 70 disposed on opposite sides of the housing, the forces are applied in a symmetrical manner on the housing and this lessons the risk of jamming.

The different inclinations of the flanks of the screw thread on the rod 30 facilitate the disengagement of the two half nuts 40A, 40B when the syringe is under pressure.

What is claimed is:

1. Device for inflating balloons comprising in combination: a syringe body and a syringe plunger slidably and rotatably movable in said syringe body, said plunger having an outer screw thread on at least a part of the length of said plunger, said device further comprising a mechanism for retaining said plunger and comprising on one hand a first half nut movable between a position in which said first half nut is spaced from said screw thread and in which said plunger is free to slide in said syringe body, and a position of engagement with said screw thread in which a free sliding of said plunger is impossible and in which said plunger can be selectively screwed and unscrewed in said syringe body, and on the other hand a control element which is mounted to be axially slidable along said syringe body, said control element comprising first coupling means for moving said first movable half nut between said two positions thereof upon the shifting of said control element, said retaining mechanism further comprising a second movable half nut disposed substantially symmetrically with said first movable half nut relative to said plunger, said second half nut being movable simultaneously with said first half nut between a position in which said second half nut is spaced from said screw thread and a position of engagement of said second half nut with said screw thread, and said second control element further comprising second coupling means associated with said second half nut for moving said second half nut, said first and second coupling means being mechanically interconnected in a region in which said control element is coupled to said first and second half nuts.

2. Device according to claim 1, wherein said first and second coupling means each comprise a part of a cam/cam follower arrangement, the complementary part of said arrangement being carried by said first and second half nuts respectively.

3. Device according to claim 2, wherein said first and second coupling means comprise for each half nut at least one slot forming a cam defined in said control element, and said first and second half nuts each comprise at least one pin forming a cam follower slidable in the respective at least one slot.

4. Device according to claim 1, wherein said first and second half nuts are movable solely laterally relative to said plunger.

5. Device according to claim 3, wherein said first and second half nuts are movable solely laterally relative to said plunger, said two slots respectively associated with said first and second half nuts are defined in a common plate of said control element, which plate extends in a direction substantially parallel to the plane of movement of said first and second half nuts.

6. Device according to claim 5, wherein said control element comprises two plates disposed laterally on opposite sides of said first and second half nuts, each plate comprising slots associated with said first and second half nuts, said half nuts each comprising on each side pins forming cam followers slidable in said slots.

7. Device according to claim 1, wherein said control element comprises two control buttons laterally symmetrically disposed on opposite sides of the length of said syringe body and manually shiftable for shifting said control element.

8. Device according to claim 6, wherein said control element comprises two control buttons laterally symmetrically disposed on opposite sides of the length of said syringe body and manually shiftable for shifting said control element, said buttons being provided at ends of connecting arms extending from said plates.

9. Device according to claim 1, wherein said screw thread has a substantially triangular cross section, the inclination relative to the perpendicular to the said plunger of front flanks of said thread cross section facing towards the end of said plunger received in said syringe body being greater than the inclination of rear flanks of said thread cross -section, the latter inclination being non-zero.

10. Device according to claim 1, wherein said syringe defines an inner chamber and a pressure gauge communicates with said chamber.

* * * * *